(12) United States Patent
Yamashita et al.

(10) Patent No.: US 8,802,032 B2
(45) Date of Patent: Aug. 12, 2014

(54) ANALYZER

(75) Inventors: Yoshihiro Yamashita, Hitachinaka (JP);
Shinya Matsuoka, Hitachinaka (JP);
Taku Sakazume, Hitachinaka (JP);
Yukinori Sakashita, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/982,768

(22) PCT Filed: Jan. 30, 2012

(86) PCT No.: PCT/JP2012/052006
§ 371 (c)(1),
(2), (4) Date: Oct. 14, 2013

(87) PCT Pub. No.: WO2012/105504
PCT Pub. Date: Aug. 9, 2012

(65) Prior Publication Data
US 2014/0030167 A1    Jan. 30, 2014

(30) Foreign Application Priority Data

Jan. 31, 2011   (JP) ................................. 2011-017382

(51) Int. Cl.
*G01N 33/00* (2006.01)
*G01N 33/48* (2006.01)
*G01N 15/06* (2006.01)

(52) U.S. Cl.
USPC ........... 422/521; 422/519; 422/501; 422/502; 422/504; 422/505; 422/509; 422/524; 436/180

(58) Field of Classification Search
USPC ......... 422/521, 519, 501, 502, 504, 505, 509, 422/524; 436/180
See application file for complete search history.

(56) References Cited

U.S. PATENT DOCUMENTS

2004/0131758 A1* 7/2004 Jung et al. .......... 427/8
2009/0238950 A1* 9/2009 Jung et al. .......... 427/8

FOREIGN PATENT DOCUMENTS

| JP | 03-195395 A | 8/1991 |
| JP | 06-148032 A | 5/1994 |
| JP | 08-015273 A | 1/1996 |
| JP | 2004-308690 A | 11/2004 |

OTHER PUBLICATIONS

Office Action issued Mar. 12, 2013, in Japanese Patent Application No. 2011-017382.
English translation of the International Preliminary Report on Patentability from International Application No. PCT/JP2012/052006, Aug. 6, 2013.

* cited by examiner

*Primary Examiner* — Brian J Sines
(74) *Attorney, Agent, or Firm* — Miles & Stockbridge P.C.

(57) ABSTRACT

This invention provides an analyzer that has a liquid dispense pipette dispensing liquids with higher accuracy and precision at higher speeds. The analyzer includes a drive mechanism having a stepping motor as a power source. The drive mechanism transmits power from a rotation output shaft of the stepping motor to a moving unit for executing a target motion via at least one power transmission unit. The amount of idling of the moving unit stemming from the stepping motor getting driven in reverse is calculated from the amount of movement of the moving unit, from the amount of pulses fed to the stepping motor, and from the amount of remaining pulses so as to perform motion control of the drive mechanism accordingly.

6 Claims, 8 Drawing Sheets

ANALYZER

TECHNICAL FIELD

The present invention relates to an analyzer equipped with a drive mechanism having a stepping motor as its power source.

BACKGROUND ART

Stepping motors are capable of being precisely controlled in rotation angle and rotation speed when supplied with computer-controllable pulse signals, so that these motors are used extensively as the mechanism drive source primarily in the field of precision apparatus. For example, automated analyzers that perform qualitative and quantitative analyses of specific components in biological samples such as blood or urine have a mechanism in which the stepping motor is used to drive the plunger of a liquid dispensing syringe so as to suck or deliver predetermined amounts of biological samples, reagents, and their reaction liquids through a liquid dispensing nozzle or the like connected with the syringe via a flow channel.

PRIOR ART LITERATURE

Patent Document 1: JP-6-148032-A

SUMMARY OF THE INVENTION

Problem to be Solved by the Invention

It has been desired that the above-mentioned analyzers have the reliability of their analysis results improved further and also have the processing capability in their analyses boosted. Thus it is an important challenge for the liquid dispense pipette of the analyzer to dispense liquids with higher accuracy and precision at higher speeds than ever.

The liquid dispense pipette is configured to drive the plunger of the syringe using the stepping motor as the power source. The liquid dispense pipette drives the syringe plunger linearly from the rotation output shaft of the stepping motor via a power transmission mechanism such as a gear and a timing belt, thereby sucking or delivering a predetermined amount of liquid through the liquid dispensing nozzle or the like connected with the syringe through the flow channel. When sucking the liquid, the stepping motor is rotated CW (clockwise) to drive downward the plunger; when delivering the liquid, the stepping motor is rotated CCW (counterclockwise) to drive upward the plunger. At the time of switching from suction to delivery or from delivery to suction of the liquid, the stepping motor is rotated in a direction opposite to a direction in which the plunger is driven. In this case, it is general practice to perform a preliminary motion to remove idling that stems from the play of the power transmission mechanism such as the gear and timing belt interposed between the rotation output shaft and a plunger drive unit, so that an accurate amount of the liquid may be kept dispensed with precision. The idling results from the dimension tolerances of individual components such as the gear and timing belt, and the difference in idling amount between analyzers and the changes in idling amount over time are difficult to suppress.

However, the preliminary motion for removing the idling constitutes a constraint on improving the processing capacity of the analyzer and is thus desired to be eliminated.

Patent Document 1 discloses a method for measuring the idling based on the actual load of the stepping motor by use of the characteristic of the motor with its drive current presenting a specific waveform with regard to load torque. However, the actual load on the stepping motor is dependent on the most loaded of the individual components that ensure drive transmission from the motor output shaft; the actual load does not necessarily coincide with, say, the plunger motion of a terminal part of the drive transmission. Thus the disclosed method cannot be applied to solving the problems with the above-mentioned analyzers. It is desired that in order to ensure the liquid dispensing performance of the analyzer, the idling amount be measured based on the plunger motion of the liquid dispensing syringe as the terminal part of drive power transmission means or on the basis of the fluid motion inside the flow channel interposed between the liquid suction/delivery nozzle and the syringe.

In view of the above-described problems, an object of the present invention is to provide an analyzer that has a liquid dispense pipette dispensing liquids with higher accuracy and precision at higher speeds.

Means for Solving the Problem

The structure for solving the above-mentioned problems is as follows.

An analyzer is provided which includes a drive mechanism having a stepping motor as a power source. The drive mechanism transmits power from a rotation output shaft of the stepping motor to a moving unit for executing a target motion via at least one power transmission unit. The amount of idling of the moving unit stemming from the stepping motor getting driven in reverse is calculated from the amount of movement of the moving unit, from the amount of pulses fed to the stepping motor, and from the amount of remaining pulses so as to perform motion control of the drive mechanism accordingly.

Effects of the Invention

With the above structure, it is possible to provide an analyzer that has a liquid dispense pipette dispensing liquids with higher accuracy and precision at higher speeds without recourse to performing preliminary motions.

MODE FOR CARRYING OUT THE INVENTION

The present invention is explained below before some embodiments thereof are described.

In a dispense pipette of the analyzer, the stepping motor for driving the plunger of a syringe for dispensing a liquid is fed with suitable pulse signals to switch from CW (clockwise) rotation to CCW (counterclockwise) rotation or from CCW (counterclockwise) rotation to CW (clockwise) rotation. Upon such switchover, the amount of movement of the plunger in the dispensing syringe is measured, and so is the amount of movement of a fluid in a flow channel interposed between a liquid suction/delivery nozzle and the syringe. Given the differences between the measured amounts on the one hand and the amount of movement calculated from the amount of supplied pulse signals on the other hand, the amount of idling is calculated which stems from the motion of a terminal part of the power transmission mechanism caused by the stepping motor getting driven in reverse. The measured amount of idling is used as the basis for setting the amount of pulse signals that are to be supplied to the stepping motor for liquid suction or delivery after the motor has been driven in reverse, whereby the preliminary motion upon switchover of the motor drive direction is omitted.

Explained below are specific means of this invention providing an analyzer equipped with a dispense pipette formed by a nozzle for sucking or delivering liquids such as a reaction fluid and a reagent as well as air, by a syringe acting as pressure difference generation means for generating a pressure difference for sucking or delivering the liquids and air, by a flow channel connecting the nozzle with the syringe, and by a stepping motor for driving the plunger of the syringe.

Described hereunder as a first example is the method for measuring the amount of idling by use of a transmissive photo interrupter sensor for measuring the plunger position in the syringe. First, the plunger is driven up to a mechanical breakpoint on the liquid delivery side, before being driven toward the liquid suction side and brought to a stop in accordance with a sensing signal from the photo interrupter installed on the suction side away from the delivery side mechanical breakpoint. With that position taken as a starting point, the plunger is fed with a suitable amount of pulse signals so as to be further driven toward the suction side. Then, the stepping motor is rotated in reverse to feed the plunger with a larger amount of pulse signals than the above amount of supplied pulse signals so that the plunger is driven toward the delivery side, and the plunger is stopped in accordance with the sensing signal from the photo interrupter. At this point, the amount of remaining pulse signals, a set value of the amount of delay pulse signals in effect from the time of sensing by the photo interrupter until the stop, and the dimensions of a photo interrupter douser as well as the sensitivity of the photo interrupter are taken into account in calculating the amount of idling stemming from the plunger motion caused by the stepping motor getting rotated in reverse.

Described hereunder as a second example is the method for measuring the amount of idling based on the amount of movement of a fluid inside the flow channel interposed between the nozzle for sucking or delivering the liquid and the syringe. An alternative method may involve using electrochemical means capable of sensing a gas and a liquid inside the flow channel. In this example, electrodes installed inside the flow channel are used to detect a predetermined amount of air bubbles inserted into the flow channel, and the syringe is driven in the same manner as when the above-mentioned photo interrupter is used. The amount of remaining pulse signals, a set value of the amount of delay pulse signals in effect from the time of electrochemical sensing until the stop, the cross-sectional area of the flow channel and the volume of air bubbles, as well as the sensitivity of electrochemical sensing are taken into account in calculating the amount of idling stemming from the movement of the fluid inside the flow channel caused by the stepping motor getting rotated in reverse.

The measured values above of the idling amount are used as the basis for setting the amount of pulse signals that are to be supplied to the stepping motor for liquid suction or delivery after the motor has been driven in reverse. This ensures that an accurate amount of the liquid is kept dispensed with precision without recourse to performing preliminary motions after the stepping motor has been driven in reverse.

Some embodiments of the present invention are explained below.

Figure 1:
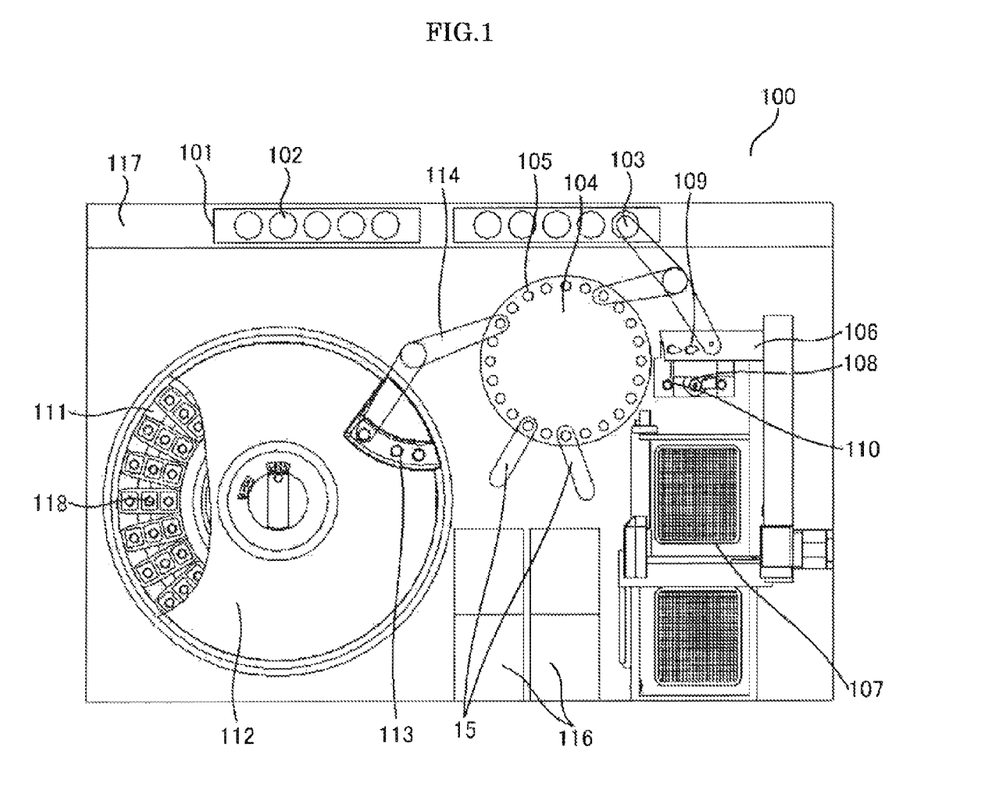
FIG. 1 is an overall structure chart of an analyzer.

Explained first in reference to FIG. 1 is an overall structure of an analyzer embodying this invention. A rack 101 of the analyzer 100 is mounted with sample containers 102 holding samples. A rack conveyor line 117 moves the sample containers up to a sample dispensing position near a sample dispensing nozzle 103. A plurality of reaction vessels 105 may be mounted on an incubator disk 104 which may be rotated to move each of the circularly arrayed reaction vessels 105 to a predetermined position. A sample dispensing tip and reaction vessel transport mechanism 106 may be moved in the X-, Y-, and Z-axis directions. The transport mechanism 106 is moved among predetermined positions of a sample dispensing tip and reaction vessel holding member 107, a reaction vessel stirring mechanism 108, a sample dispensing tip and reaction vessel disposal hole 109, a sample dispensing tip attaching position 110, and the incubator disk 104, so as to transport the sample dispensing tips and reaction vessels. A plurality of unused reaction vessels and a plurality of sample dispensing tips are mounted on the sample dispensing tip and reaction vessel holding member 107. The sample dispensing tip and reaction vessel transport mechanism 106 is moved to above the sample dispensing tip and reaction vessel holding member 107, lowered to hold an unused reaction vessel before coming upward, moved to above a predetermined position of the incubator disk 104, and lowered to set the reaction vessel in place. Then the sample dispensing tip and reaction vessel transport mechanism 106 is moved to above the sample dispensing tip and reaction vessel holding member 107, lowered to hold an unused sample dispensing tip before coming upward, moved to above the sample dispensing tip attaching position 110, and lowered to set the sample dispensing tip in place. The sample dispensing nozzle 103 may be moved rotatably as well as up and down. After being moved rotatably to above the sample dispensing tip attaching position 110, the sample dispensing nozzle 103 is lowered to press a sample dispensing tip into place of the head of the nozzle 103. The sample dispensing nozzle 103 mounted with the sample dispensing tip is moved to above the sample container 102 placed on the transport rack 101, before being lowered to suck a predetermined amount of the sample held in the sample container 102. After sucking the sample, the sample dispensing nozzle 103 is moved to above the incubator disk 104 and lowered to deliver the sample into an unused reaction vessel 105 held on the incubator disk 104. Following delivery of the sample, the sample dispensing nozzle 103 is moved to above the sample dispensing tip and reaction vessel disposal hole 109 to discard the used sample dispensing tip through the disposal hole. A plurality of reagent vessels 118 are mounted on a reagent disk 111. A reagent disk cover 112 is provided over the reagent disk 111 to keep the interior of the reagent disk 111 at a constant temperature. Part of the reagent disk cover 112 has a reagent disk cover opening 113. A reagent dispensing nozzle 114 may be moved rotatably as well as up and down. After being moved rotatably to above the opening 113 of the reagent disk cover 112, the reagent dispensing nozzle 114 is lowered to dip its head into a reagent in a suitable reagent vessel to suck a predetermined amount of the reagent therefrom. Then after being moved up, the reagent dispensing nozzle 114 is moved rotatably to above a predetermined position of the incubator disk 104 to deliver the reagent into the reaction vessel 105. With the sample and the reagent delivered therein, the reaction vessel 105 is moved to a predetermined position by rotation of the incubator disk 104, before being transported to the reaction vessel stirring mechanism 108 by the sample dispensing tip and reaction vessel transport mechanism 106. The reaction vessel stirring mechanism 108 gives a rotary movement to the reaction vessel to stir the sample and reagent therein for mixture. After being stirred, the reaction vessel is returned to the predetermined position of the incubator disk 104 by the sample dispensing tip and reaction vessel transport mechanism 106. A reaction fluid suction nozzle 115 may be moved rotatably as well as up and down. Over the incubator disk 104, the reaction fluid suction nozzle 115 is moved to above the reaction vessel 105 in which the sample and reagent have been dispensed and are allowed to react with one another for a predetermined reaction time. The reaction fluid suction nozzle 115 is then lowered to suck a reaction fluid from inside the reaction vessel 105. The reaction fluid sucked by the reaction fluid suction nozzle 115 is analyzed by a detection unit 116. The reaction vessel 105 from which the reaction fluid has been sucked is moved to a predetermined position by rotation of the incubator disk 104. The reaction vessel 105 is then moved by the sample dispensing tip and reaction vessel transport mechanism 106 from the incubator disk 105 to above the sample dispensing tip and reaction vessel disposal hole 109 and discarded through the disposal hole.

Figure 2:
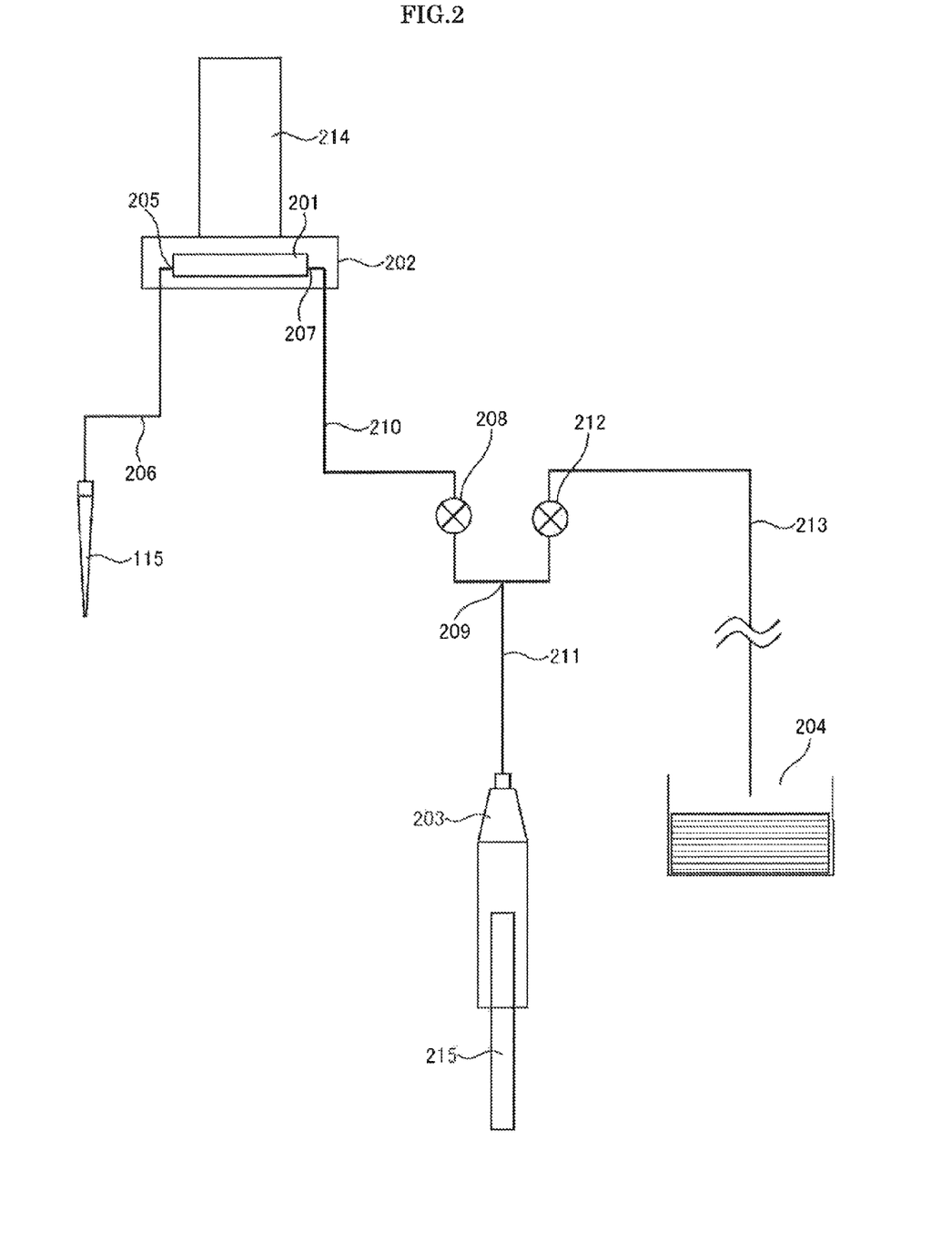
FIG. 2 is a structure chart of flow channels in a detection system.

Next, a conventional flow of analysis is explained using the structure chart of detection flow channels in FIG. 2. The reaction fluid suction nozzle 115 for sucking or delivering a liquid and air, a flow cell detector 202 for detecting a measuring object, a syringe 203 and a plunger 215 for generating a pressure difference therebetween for sucking or delivering the liquid and air, and a drain 204 for draining the liquid and air are furnished with a first flow channel 206 connecting the nozzle with an inlet connection part 205 of the flow cell detector, a second flow channel 210 connecting an outlet connection part 207 of the flow cell detector with a bifurcation part 209 via a first valve 208, a third flow channel 211 connected with the syringe via the bifurcation part 209, and a fourth flow channel 213 connecting the bifurcation part 209 with the drain 204 via a second valve 212. In this flow channel structure, the liquid and air are sucked or delivered through the reaction fluid suction nozzle 114 when the plunger 215 is moved up and down and the first valve 208 and second valve 212 are opened and closed in switching fashion. The analyzing cycle of the analyzer including this flow channel structure proceeds as follows: In a reaction fluid in which a sample containing the measuring object is mixed with a reagent containing a detection label and a reagent containing magnetic particles, a compound made up of the measuring object, detection label and magnetic particles is formed. The reaction fluid suction nozzle 114 is inserted into the container holding the reaction fluid. The first valve 208 interposed between the outlet connection part 207 of the flow cell detector 202 and the bifurcation part 209 is opened and the second valve 212 interposed between the bifurcation part 209 and the drain 204 is closed so as to move the plunger 215 in the syringe 203 toward the suction side and thereby suck the reaction fluid into the flow cell. Inside the flow cell, the compound in the reaction fluid is magnetically absorbed by a detection part 201. With the reaction fluid suction nozzle 114 taken out of the reaction fluid container, the plunger 215 in the syringe 203 is moved toward the suction side in order to suck the reaction fluid and an air segment that separates the fluid from a detection reaction reagent to be sucked next. Then the first valve 208 is closed and the second valve 212 is opened to move the plunger 215 in the syringe 203 toward the delivery side. This motion drains the liquid and gas remaining in the third flow channel 211 connecting the bifurcation part 209 with the syringe 203 into the drain 204. As a preliminary motion (A) preparatory to sucking the next liquid, the plunger 215 in the syringe 203 is moved toward the suction side. The reaction fluid suction nozzle 114 is then inserted into the container holding the detection reaction reagent. The first valve 208 is opened and the second valve 212 is closed to move the plunger 215 in the syringe 203 toward the suction side and thereby suck the detection reaction reagent. From the surface of the magnetic particles absorbed magnetically by the detection part 201 of the flow cell detector 202, the reaction fluid component is removed and replaced with the detection reaction reagent to induce a detection reaction. Given the detection reaction, a detector 214 connected with the flow cell detector 202 detects a detection reaction signal. Then the first valve 208 is closed and the second valve 212 is opened to move the plunger 215 in the syringe 203 toward the delivery side. This motion drains the liquid and air remaining in the flow channel 211 connecting the bifurcation part 209 with the syringe 203 into the drain 204. As another preliminary motion (B) preparatory to sucking the next liquid, the plunger 215 in the syringe 203 is moved toward the suction side. Then with the reaction fluid suction nozzle 114 taken out of the detection reaction reagent container, the first valve 208 is opened and the second valve 212 is closed to move the plunger 215 in the syringe 203 toward the suction side in order to suck the detection reaction fluid and an air segment that separates the fluid from a cleaning reagent to be sucked next. The reaction fluid suction nozzle 114 is then inserted into the container holding the cleaning reagent. The first valve 208 is opened and the second valve 212 is closed to move the plunger 215 in the syringe 203 toward the suction side so as to suck the cleaning reagent and clean the detection part 201 of the flow cell detector 202 thereby. At this point, the reaction fluid suction nozzle 114 is removed from and inserted into the cleaning reagent container alternately to suck both the cleaning reagent and the air segment in alternating fashion, whereby the efficiency in cleaning the detection part 201 is improved. Then the first valve 208 is closed and the second valve 212 is opened to move the syringe 203 toward the delivery side. This motion drains the fluid and gas remaining in the third flow channel 211 connecting the bifurcation part 209 with the syringe into the drain 204. As a further preliminary motion (C) preparatory to sucking the next liquid, the plunger 215 in the syringe 203 is moved toward the suction side. Then with the reaction fluid suction nozzle 114 taken out of the cleaning reagent container, the first valve 208 is opened and the second valve 212 is closed to move the plunger 215 in the syringe 203 toward the section suction in order to suck the cleaning reagent and an air segment that separates the reagent from a detection preparation reagent to be sucked next. The reaction fluid suction nozzle 114 is then inserted into the container holding the preparation reagent. The first valve 208 is opened and the second valve 212 is closed to move the plunger 215 in the syringe 203 toward the suction side so as to suck the detection preparation reagent. Then with the reaction fluid suction nozzle 114 moved toward the reaction fluid container and just before the nozzle is inserted into the reaction fluid, another preliminary motion (D) is performed which involves closing the first valve 208 and opening the second valve 212 to move the plunger 215 in the syringe 203 toward the delivery side. Thereafter, the first valve 208 is opened and the second valve 212 is closed to exclude the mixture of the detection preparation reagent with an air segment that separates the reagent from the reaction fluid to be sucked next. This allows the reaction fluid to be sucked next to efficiently disperse throughout the detection preparation reagent inside the flow channel ranging from the reaction fluid suction nozzle 114 to the flow cell detector 202, whereby subsequent detection reaction is promoted. Then another preliminary motion (E) is performed which involves closing the first valve 208 and opening the second valve 212 to move the plunger 215 in the syringe 203 toward the suction side preparatory to sucking the reaction fluid.

In the conventional flow of analysis, as described above, reversing the plunger drive direction in the syringe requires performing the preliminary motions (A) through (E) preparatory to driving the plunger. This constitutes a hindrance to improving the efficiency of the analyzing cycle.

Figure 3:
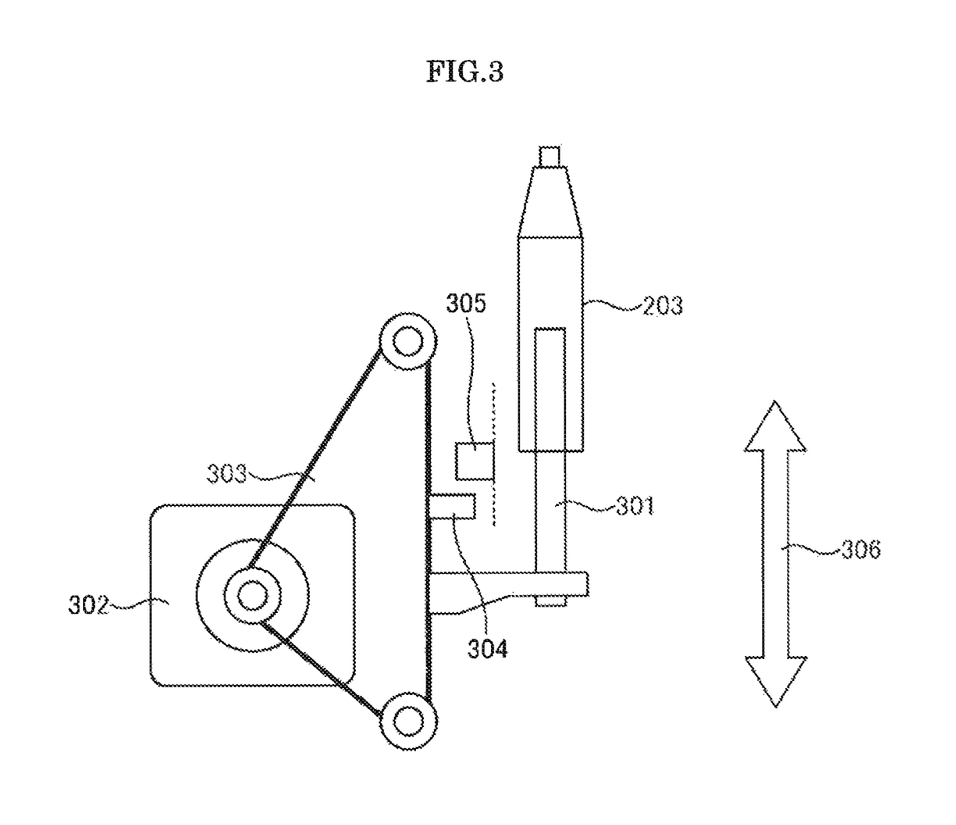
FIG. 3 is a structure chart of a syringe unit.

What follows is an explanation of the method for measuring idling based on the drive amount of the plunger. As shown in the structure chart of the syringe unit in FIG. 3, a liquid or gas is delivered from or sucked into the syringe 203 by driving the plunger 215 in the up and down direction 301. The drive power is transmitted from a stepping motor 302 to the plunger 215 by way of a gear and a belt 303. A photo interrupter douser 304 is fixed to a predetermined position of the belt 303. Meanwhile, to a non-moving unit serving as the reference position, a photo interrupter sensor 305 is fixed in a manner letting the douser 304 pass through. This allows the reference position of the plunger 215 to be detected.

Figure 4:
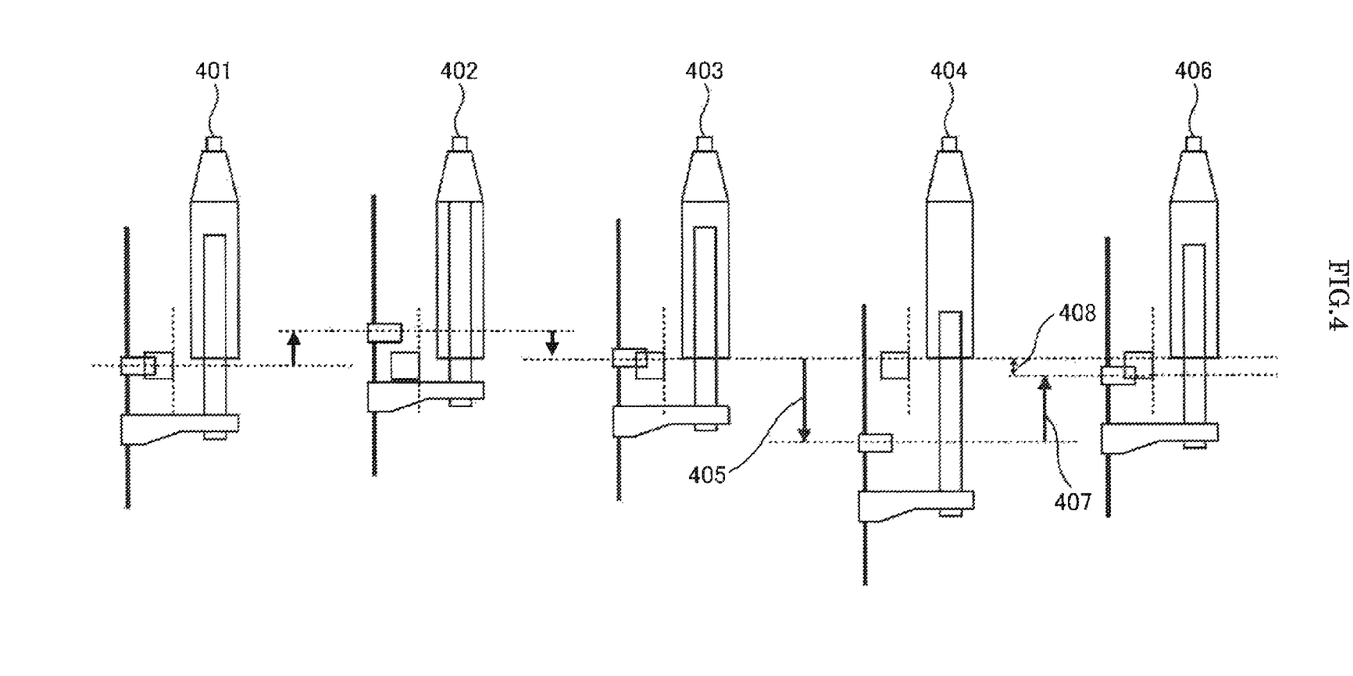
FIG. 4 is a flow diagram of the motion of measuring the amount of idling.

FIG. 4 gives a schematic view showing plunger positions in effect when the photo interrupter sensor for sensing the reference position of the plunger is used to measure the amount of idling. (1) From a reference position 401 in which the douser is inserted into the photo interrupter sensor, (2) the plunger is driven in the delivery direction up to a position 402 where the douser is detached from the photo interrupter sensor. (3) Thereafter, the plunger is driven in the suction direction up to a position 403 where the douser is again inserted into the photo interrupter sensor. At this point, the plunger is stopped immediately upon sensing (from brightness to darkness) by the photo interrupter sensor. (4) Then a suitable amount of pulses (a) 405 is supplied so as to drive the plunger in the suction direction up to a position 404 where the plunger is stopped after the supplied pulses have all been consumed. (5) After this, a suitable amount of pulses (b) 406 is supplied so as to drive in reverse the plunger in the delivery direction up to a position 407 where the plunger is stopped immediately upon sensing (from brightness to darkness) by the photo interrupter sensor. The amount of the pulses supplied above is to be adjusted in such a manner that the number (c) of pulses remaining after the plunger was driven in reverse and stopped may become positive. Also, there are provided correction pulses (e) 408 for correcting the position in which the plunger moved in the suction direction is stopped by the photo interrupter sensor, and the position in which the plunger moved in the delivery direction is stopped by the photo interrupter sensor. The correction pulses (e) 408 are primarily dependent on the length of the douser in the plunger drive direction, on the sensitivity of the photo interrupter sensor sensing the douser, and on the amount of delay pulses ranging from sensing to a stop.

From the foregoing description, the amount ($\alpha$) of idling with reference to the plunger drive amount is calculated using the following expression (1):

$$\alpha = (b - c + e) - a \qquad (1)$$

Figure 5:
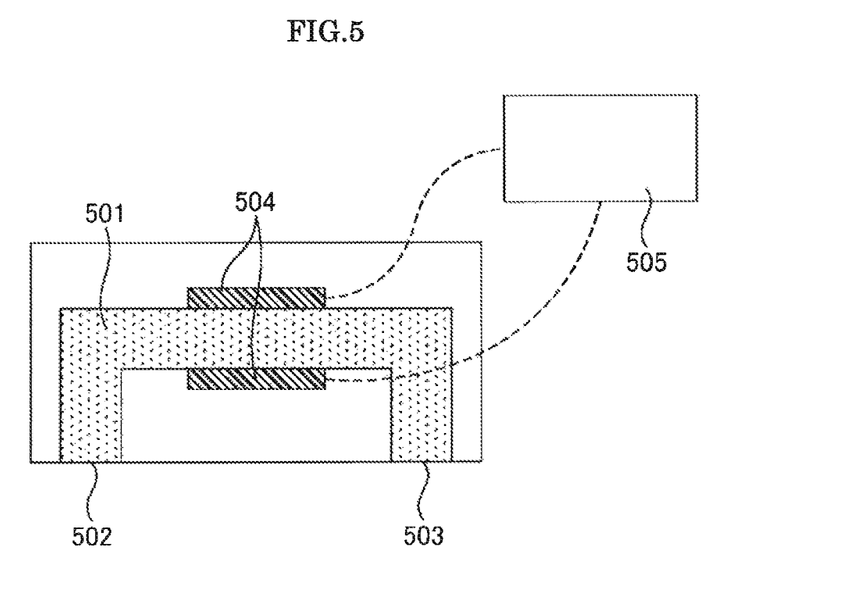
FIG. 5 is a structure chart of a flow cell.

Explained below in reference to FIGS. 5 and 6 is the method for measuring the amount of idling by use of a gas-liquid fluid flowing in the flow channel.

FIG. 5 schematically shows the flow cell of the analyzer. The flow cell detector is furnished with a flow channel 501, a solution inlet 502, and a solution outlet 503 through which a solution containing the measuring object is allowed to flow. Electrodes 504 are installed inside the flow channel and are supplied with a predetermined voltage from voltage application/current measurement means 505, and the current flowing between the electrodes is measured.

Figure 6A:
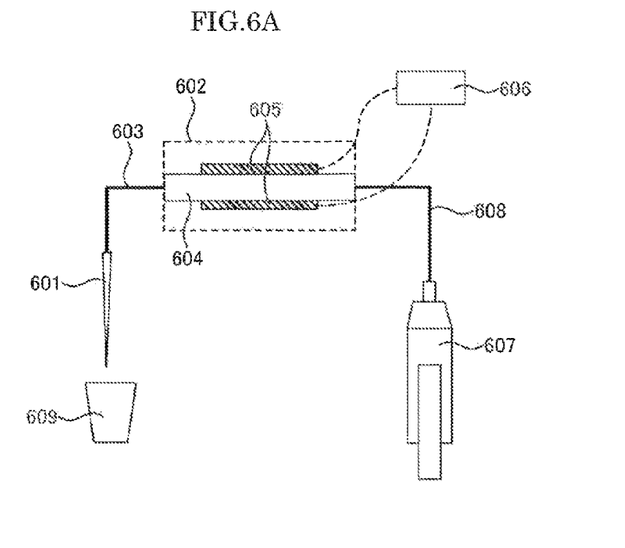
FIG. 6A is a flow diagram of the motion of measuring the amount of idling through measurement of a gas-liquid flow.

The procedure for measuring the amount of idling with the above-described structure is explained here in reference to FIGS. 6A through 6H. FIG. 6A schematically shows only a portion relevant to the explanation in the flow channel structure of the analyzer. The schematic structure chart includes a nozzle 601, a flow cell 602, a flow channel 603 connecting the nozzle with the flow cell, an intra-flow cell flow channel 604, electrodes 605, voltage application/current measurement means 606, a syringe 607, a flow channel 608 connecting the flow cell with the syringe, and a reagent container 609. Although the nozzle drive means is not shown in this chart, the nozzle can be driven up and down by suitable drive means. Although the syringe drive means is also not shown, the syringe can be moved for suction and delivery by suitable drive means. The reagent container holds a reagent containing an electrolyte.

Figure 6B:
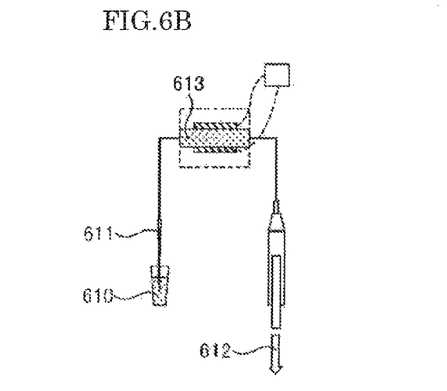
FIG. 6B is a flow diagram of the motion of measuring the amount of idling through measurement of a gas-liquid flow.

First, as shown in FIG. 6B, the syringe is moved for suction (indicated by 612) with the nozzle dipped in a reagent solution 610 (indicated by 611), so as to fill the entire flow channel with the reagent solution (indicated by 613).

A voltage is applied across the electrodes using the voltage application/current measurement means, and the current flowing between the electrodes is measured.

Figure 6C:
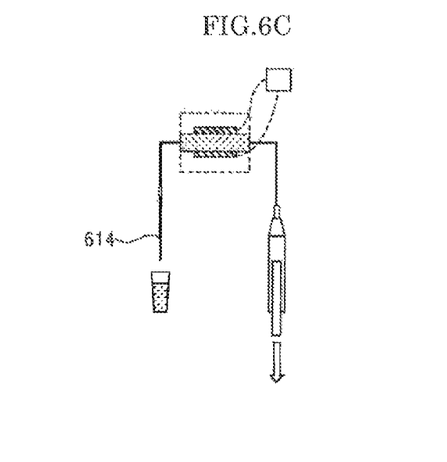
FIG. 6C is a flow diagram of the motion of measuring the amount of idling through measurement of a gas-liquid flow.
Figure 6D:
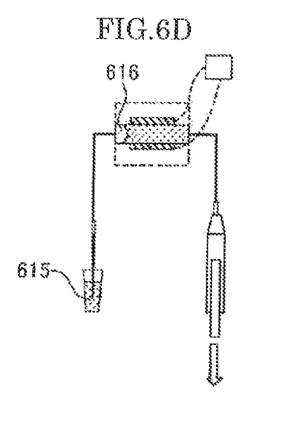
FIG. 6D is a flow diagram of the motion of measuring the amount of idling through measurement of a gas-liquid flow.

Next, as shown in FIGS. 6C and 6D, the nozzle is lifted from the reagent container into the air (indicated by 614). Upon elapse of a predetermined time period, the nozzle is again lowered into the reagent container (indicated by 615). During this time, the syringe is kept moved for suction at a constant speed. This operation introduces a predetermined amount of air 616 into the flow channel.

Figure 6E:
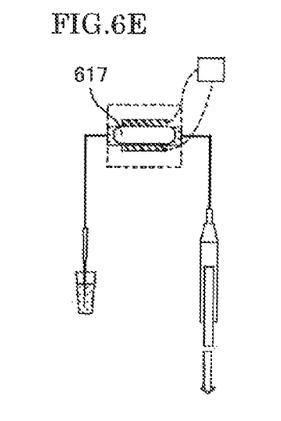
FIG. 6E is a flow diagram of the motion of measuring the amount of idling through measurement of a gas-liquid flow.

As the syringe is kept moved for suction, as shown in FIG. 6E, the introduced air reaches the electrodes (indicated by 617). At this time, the space between the electrodes is filled with the air so that no current flows therebetween.

Figure 6F:
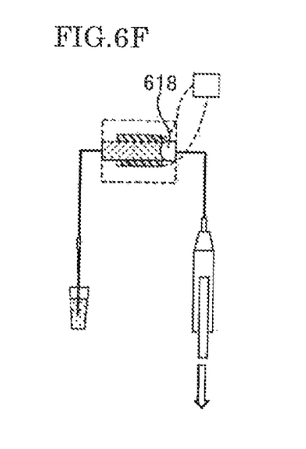
FIG. 6F is a flow diagram of the motion of measuring the amount of idling through measurement of a gas-liquid flow.

As the syringe is kept moved further for suction, as shown in FIG. 6F, the reagent solution introduced following the air reaches the electrodes so that the air between the electrodes is replaced with the reagent solution (indicated by 618). This causes the current to start flowing again. When the current value in effect before the air reaches the electrodes is recorded in advance and compared with the current value measured after the air has passed, the time period in which all air has moved past the electrodes can be estimated. That time is identified as t1.

Figure 6G:
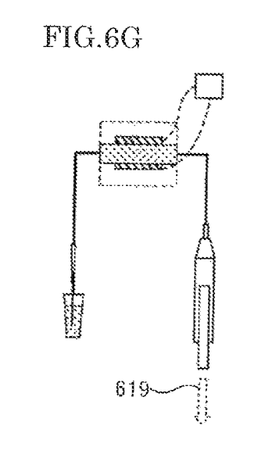
FIG. 6G is a flow diagram of the motion of measuring the amount of idling through measurement of a gas-liquid flow.

Then as shown in FIG. 6G, following the verification that all air has moved past the electrodes, the syringe is moved further for suction for a predetermined time period (t2), before it is stopped for the moment (indicated by 619).

Figure 6H:
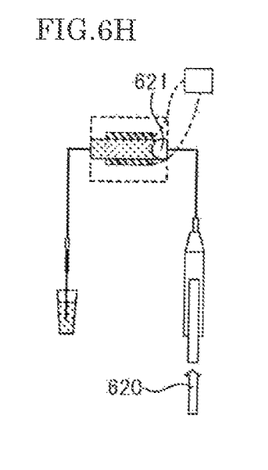
FIG. 6H is a flow diagram of the motion of measuring the amount of idling through measurement of a gas-liquid flow.

Then as shown in FIG. 6H, the syringe is driven in the delivery direction at the same speed as the suction motion above (indicated by 620). This causes the air that moved past the electrodes to return to the electrodes (indicated by 621). As the air starts getting introduced between the electrodes, the current value begins to drop. In comparison with the previously recorded current in effect when the space between the electrodes was filled with the solution, the time that elapses from the time the syringe starts to be driven in the delivery direction until a drop in the current is detected is identified as t3.

Explained next is the method for calculating the amount of idling using the measurements t1, t2 and t3 taken through the above operations.

The time it takes the air that moved past the electrodes to advance toward the syringe side is represented by t2 as explained above. The time required for the air brought to that position to be again moved up to the electrodes by the delivery motion of the syringe is represented by t3 as described above.

If it is assumed here that idling does not exist and that all the amount of driving the syringe is used to drive the fluid, there is no difference between t2 and t3. In practice, however, there exists the idling of the syringe and therefore there occurs a difference between t2 and t3. The difference between t2 and t3 (t3−t2) is the time during which the syringe motion was not transmitted to drive the solution because of idling. If "u" represents the pulse velocity for the syringe to suck and deliver air, the amount of idling ($\alpha$) is calculated using the following expression (2):

$$\alpha = (t3-t2)/u \quad (2)$$

The value $\alpha$ above constitutes the amount of idling in reference to the behavior of the gas-liquid flow in the flow channel.

According to the above-described method, the idling value ($\alpha$) calculated before an analyzing process or during analysis preparations is added to the amount of supplied pulses for driving the syringe for suction or delivery after the syringe drive direction is reversed. This makes it possible to omit the above-described preliminary motions (A) through (E) preparatory to driving the syringe and to improve the efficiency of the analyzing cycle and boost processing capability while ensuring the reliability of analytical performance.

DESCRIPTION OF REFERENCE NUMERALS

100 Analyzer
101 Rack
102 Sample container
103 Sample dispensing nozzle
104 Incubator disk
105 Reaction vessel
106 Sample dispensing tip and reaction vessel transport mechanism
107 Sample dispensing tip and reaction vessel holding member
108 Reaction vessel stirring mechanism
109 Sample dispensing tip and reaction vessel disposal hole
110 Sample dispensing tip attaching position
111 Reagent disk
112 Reagent disk cover
113 Reagent disk cover opening
114 Reagent dispensing nozzle
115 Reaction fluid suction nozzle
116 Detection unit
117 Rack conveyor line
118, 609 Reagent vessel
201 Detection part
202 Flow cell detector
203, 607 Syringe
204 Drain
205 Flow cell detector inlet connection part
206 First flow channel
207 Flow cell detector outlet connection part
208 First valve
209 Bifurcation part
210 Second flow channel
211 Third flow channel
212 Second valve
213 Fourth flow channel
214 Detector
215 Plunger
301 Up and down direction
302 Stepping motor
303 Belt
304 Douser
305 Photo interrupter sensor
401 Reference position where douser is inserted into photo interrupter sensor
402 Position where douser is detached from photo interrupter sensor
403 Position where douser is again inserted into photo interrupter sensor
404 Position where motion is stopped after all supplied pulses have been consumed
405 Predetermined amount of pulses (a)
406 Predetermined amount of pulses (b)
407 Position where motion is immediately stopped upon sensing (from brightness to darkness) by photo interrupter sensor
408 Correction pulses (e)
501 Intra-flow cell flow channel
502 Solution inlet
503 Solution outlet
504, 605 Electrode
505 Voltage application/current measurement means
601 Nozzle
602 Flow cell
603 Flow channel that connects nozzle with flow cell
604 Intra-flow cell flow channel
606 Voltage application/current measurement means
608 Flow channel that connects flow cell with syringe
610 Reagent solution
611, 615 State in which nozzle is dipped into reagent solution
612 Syringe suction motion
613 State in which space between electrodes is filled with reagent solution
614 State in which nozzle is lifted into the air
616 Air introduced into flow channel
617 State in which space between electrodes is filled with air
618 State in which all air has moved past electrodes
619 Syringe motion stopped
620 Syringe delivery motion
612 State in which air begins to reach electrodes

The invention claimed is:
1. A dispensing apparatus comprising:
a syringe having a plunger driven by a stepping motor as a power source;
a nozzle for sucking gas and liquid with the driving motion of said syringe;
a flow channel for connecting the nozzle with the syringe;

at least one power transmission unit for transmitting power from a rotation output shaft of the stepping motor to the plunger; and an electrode for detecting a change of a current or voltage for detecting a boundary surface between a gas layer and a liquid layer in the flow channel when the plunger is driven in case that a gas and liquid are in the flow channel, wherein the amount of idling of the stepping motor before and after the stepping motor driven in reverse direction is calculated on the basis of a time at the boundary surface between a gas layer and a liquid layer passing through the electrode and the amount of the movement of the plunger.

2. The dispensing apparatus according to claim 1, wherein a motion control of a drive mechanism is performed on the basis of the calculated the amount of idling.

3. The dispensing apparatus according to claim 1, wherein a method for controlling the drive mechanism based on the amount of idling at the stepping motor driven in reverse direction involves adding a movement reflecting the idling amount to the driving motion of the syringe after the stepping motor has been driven in reverse.

4. An analyzer comprising the dispensing apparatus according to claim 1, wherein the electrode includes a function for inducing detection reaction for an analysis.

5. An analyzer comprising the dispensing apparatus according to claim 2, wherein the electrode includes a function for inducing detection reaction for an analysis.

6. An analyzer comprising the dispensing apparatus according to claim 3, wherein the electrode includes a function for inducing detection reaction for an analysis.

* * * * *